United States Patent
Boeing et al.

(10) Patent No.: US 9,200,216 B2
(45) Date of Patent: Dec. 1, 2015

(54) PROCESS FOR OLIGOMERIZING OLEFINS

(75) Inventors: Christian Boeing, Cologne (DE); Dietrich Maschmeyer, Recklinghausen (DE); Markus Winterberg, Datteln (DE); Stefan Buchholz, Hanau (DE); Berthold Melcher, Erlangen (DE); Marco Haumann, Velden (DE); Peter Wasserscheid, Erlangen (DE)

(73) Assignee: EVONIK DEGUSSA GmbH, Essen (DE)

( * ) Notice: Subject to any disclaimer, the term of this patent is extended or adjusted under 35 U.S.C. 154(b) by 717 days.

(21) Appl. No.: 13/394,827

(22) PCT Filed: Aug. 12, 2010

(86) PCT No.: PCT/EP2010/061770
§ 371 (c)(1),
(2), (4) Date: Oct. 16, 2012

(87) PCT Pub. No.: WO2011/029691
PCT Pub. Date: Mar. 17, 2011

(65) Prior Publication Data
US 2013/0030233 A1    Jan. 31, 2013

(30) Foreign Application Priority Data
Sep. 8, 2009  (DE) .................... 10 2009 029 284

(51) Int. Cl.
*C10G 50/00* (2006.01)
*B01J 31/02* (2006.01)
(Continued)

(52) U.S. Cl.
CPC ............. *C10G 50/00* (2013.01); *B01J 31/0274* (2013.01); *B01J 31/0279* (2013.01);
(Continued)

(58) Field of Classification Search
CPC .. C07C 2531/22; C07C 2/30; C07C 2531/14; C07C 2523/04; C07C 2/34; B01J 2531/824; B01J 31/24; B01J 31/2409; B01J 2531/822; C08G 67/02

USPC .......................................... 585/511; 502/162
See application file for complete search history.

(56) References Cited

U.S. PATENT DOCUMENTS 3,592,869 A * 7/1971 Cannell et al. ................ 585/512
5,064,805 A * 11/1991 Otowa ........................ 502/427
(Continued)

FOREIGN PATENT DOCUMENTS

CN        1868588 A    11/2006
CN      101200404 A     6/2008
(Continued)

OTHER PUBLICATIONS

Haynes, CRC Handbook of Chemistry and Physics, 95th edition, 2014 Internet Version, W. M. Haynes, editor—month unknown.*
(Continued)

*Primary Examiner* — Renee E Robinson
*Assistant Examiner* — Aaron Pierpont
(74) *Attorney, Agent, or Firm* — Oblon, McClelland, Maier & Neustadt, L.L.P.

(57) ABSTRACT

The invention provides a catalyst system composed of:
a) a support material selected from at least one of the following materials: silicon dioxide, aluminum oxide, magnesium oxide, zirconium oxide and mixed oxides thereof, carbon nanotubes;
b) an ionic liquid;
c) a catalytically active composition comprising nickel;
d) an activator selected from the group of Lewis acids with alkylating properties.
Additionally provided is the use of the catalyst systems of the invention in the oligomerization of unsaturated hydrocarbon mixtures.

17 Claims, 1 Drawing Sheet

Batch stirred tank reactor

(51) Int. Cl.
  *B01J 31/14*   (2006.01)
  *B01J 31/22*   (2006.01)
  *B01J 31/24*   (2006.01)
  *B01J 31/26*   (2006.01)
  *B82Y 30/00*   (2011.01)
  *C07C 2/32*    (2006.01)
  *C07C 2/36*    (2006.01)
  *B01J 21/04*   (2006.01)
  *B01J 21/06*   (2006.01)
  *B01J 21/08*   (2006.01)
  *B01J 21/10*   (2006.01)
  *B01J 21/18*   (2006.01)
  *B01J 35/02*   (2006.01)
  *B01J 35/10*   (2006.01)

(52) U.S. Cl.
  CPC ......... *B01J 31/0281* (2013.01); *B01J 31/0284* (2013.01); *B01J 31/0288* (2013.01); *B01J 31/0292* (2013.01); *B01J 31/143* (2013.01); *B01J 31/2234* (2013.01); *B01J 31/2404* (2013.01); *B01J 31/26* (2013.01); *B82Y 30/00* (2013.01); *C07C 2/32* (2013.01); *C07C 2/36* (2013.01); *B01J 21/04* (2013.01); *B01J 21/066* (2013.01); *B01J 21/08* (2013.01); *B01J 21/10* (2013.01); *B01J 21/18* (2013.01); *B01J 21/185* (2013.01); *B01J 35/023* (2013.01); *B01J 35/1019* (2013.01); *B01J 35/1042* (2013.01); *B01J 2231/20* (2013.01); *B01J 2231/323* (2013.01); *B01J 2531/847* (2013.01); *C07C 2531/24* (2013.01); *C10G 2300/1088* (2013.01); *C10G 2300/70* (2013.01); *C10G 2400/22* (2013.01)

(56) References Cited

U.S. PATENT DOCUMENTS

| | | | |
|---|---|---|---|
| 5,849,972 A * | 12/1998 | Vicari | G01J 23/755 502/337 |
| 6,706,657 B2 * | 3/2004 | Commereuc et al. | 502/164 |
| 6,777,584 B2 * | 8/2004 | Patil et al. | 585/511 |
| 7,193,116 B2 | 3/2007 | Moeller et al. | |
| 7,317,130 B2 | 1/2008 | Möller et al. | |
| 7,495,134 B2 | 2/2009 | Hess et al. | |
| 7,910,786 B2 | 3/2011 | Winterberg et al. | |
| 7,919,662 B2 | 4/2011 | Winterberg et al. | |
| 7,968,758 B2 | 6/2011 | Winterberg et al. | |
| 2002/0169071 A1 * | 11/2002 | Sauvage et al. | 502/150 |
| 2003/0181775 A1 | 9/2003 | Lecocq et al. | |
| 2005/0159299 A1 * | 7/2005 | Rodriguez et al. | 502/103 |
| 2009/0264691 A1 | 10/2009 | Jess et al. | |
| 2011/0118523 A1 | 5/2011 | Winterberg et al. | |
| 2011/0130595 A1 | 6/2011 | Lueken et al. | |
| 2012/0197025 A1 | 8/2012 | Christiansen et al. | |

FOREIGN PATENT DOCUMENTS

| | | |
|---|---|---|
| DE | 10 2006 019 460 | 10/2007 |
| JP | 11-71304 A | 3/1999 |
| JP | 2008-540107 A | 11/2008 |
| WO | 98 47616 | 10/1998 |
| WO | WO 01/32308 A1 | 5/2001 |
| WO | WO 2006/122563 A1 | 11/2006 |

OTHER PUBLICATIONS

Yao, C.; Pitner, W. R.; Anderson, J. L. "Ionic Liquids Containing the Tris(pentafluoroethyl)trifluorophosphate Anion: a New Class of Highly Selective and Ultra Hydrophobic Solvents for the Extraction of Polycyclic Aromatic Hydrocarbons Using Single Drop Microextraction", Anal. Chem. (2009), 81, 5054-5063.*

"CRC Handbook of Chemistry and Physics", 95th edition, 2015 Internet Version, W. M. Haynes, editor (p. 1-553).*

Fan, et al., "Preparation of Ni/SiO$_2$ catalyst in ionic liquids for hydrogenation", Front. Chem. Eng. China, vol. 2 (1), p. 63-68, XP009138431. (2008).

Virtanen, et al., "Towards one-pot synthesis of menthols from citral: Modifying Supported Ionic Liquid Catalysts (SILCAs) with Lewis and Bronsted acids", Journal of Catalysis, vol. 263, pp. 209-219, XP026043758. (2009).

International Search Report issued on Sep. 20, 2010 in PCT/EP10/61770 filed on Aug. 12, 2010.

U.S. Appl. No. 13/381,680, filed Feb. 14, 2012, Winterberg, et al.
U.S. Appl. No. 13/822,650, filed Mar. 13, 2013, Franke, et al.
U.S. Appl. No. 13/582,265, filed Mar. 11, 2013, Christiansen, et al.
U.S. Appl. No. 13/883,808, filed May 7, 2013, Franke, et al.
U.S. Appl. No. 13/808,010, filed Mar. 15, 2013, Boeing, et al.

* cited by examiner

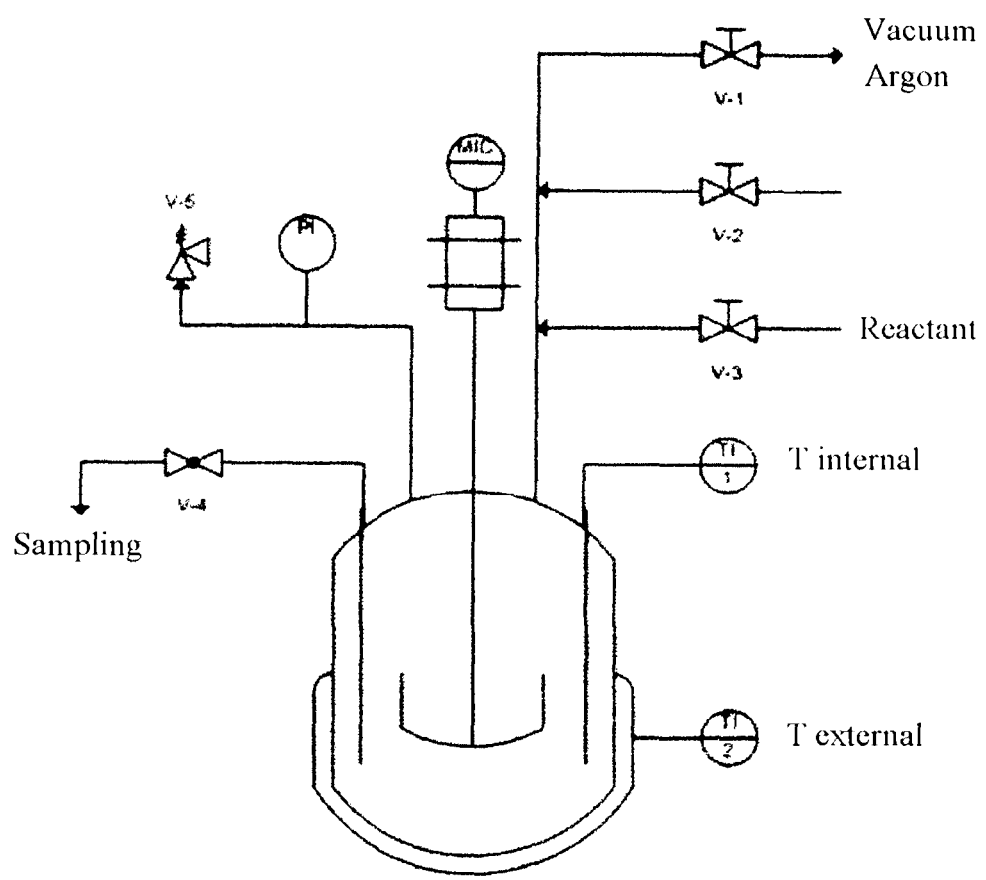
Batch stirred tank reactor

PROCESS FOR OLIGOMERIZING OLEFINS

The present invention relates to a multi-component catalyst system and to its use in a process for oligomerizing $C_3$ to $C_5$ olefins from olefin-containing hydrocarbon mixtures.

The low molecular mass oligomers of olefins, more particularly the dimers of $C_3$-$C_5$ olefins, are intermediates which are used, for example, for preparing aldehydes, carboxylic acids and alcohols. The $C_8$ olefins formed by oligomerization from linear butenes can be reacted by hydroformylation and subsequent hydrogenation to give the corresponding nonanols, which in turn are used primarily for preparing plasticizers.

Starting materials which can be used for the preparation of the oligomers include pure olefins with a double bond in a 1 position, pure olefins with an internal double bond, and mixtures of these olefins. Particularly economic processes for preparing the oligomers are those using mixtures of α-olefin and olefins with an internal double bond, and optionally paraffins.

As far as the use of the products prepared by oligomerization is concerned, their degree of branching is frequently a criterion. One measure of the degree of branching is the iso index. It is defined by the number of branches per molecule. For example, linear octenes (n-octenes) have an iso index of 0, methyl heptenes an iso index of 1, and dimethyl hexenes an iso index of 2. The calculation of the iso index of mixtures takes account of the mass fractions of the individual groups of compounds. The lower the iso index of a mixture, the more linear, on average, the compounds present therein.

The iso index of an olefin mixture defines the lowest possible degree of branching of the derivative products, and hence is a co-determinant of their profile of performance properties.

As far as the preparation of nonanols by hydroformylation of a $C_8$ olefin mixture and subsequent hydrogenation is concerned, high linearity on the part of the mixture is an advantage, since the linear olefins react more rapidly and selectively than the branched olefins and hence give rise to higher yields. The use of a $C_8$ olefin mixture with a low iso index produces a more linear nonanol mixture than when a more branched $C_8$ olefin mixture is used. A low iso index on the part of nonanol mixtures enhances the performance properties of the plasticizers prepared from them, particularly the viscosity. Thus, for example, in the case of a nonyl phthalate mixture, a low iso index is beneficial in respect of a low volatility and a better low-temperature fracture temperature on the part of the unplasticized PVC produced using the plasticizer.

The oligomerization of olefins, especially of propene and butenes, is carried out industrially either in homogeneous phase, over a molecular catalyst, or heterogeneously, over a solid catalyst.

A regime with homogenous catalysis is described, for example, by A. Chauvel and G. Lefebvre in Petrochemical Processes, volume 1, Editions Technip 1989, pp. 183-187. One process with homogeneous catalysis that is practised worldwide is the oligomerization with soluble molecular nickel complexes, known as the DIMERSOL process (see Yves Chauvin, Helene Olivier, in "Applied Homogeneous Catalysis with Organometallic Compounds", edited by Boy Cornils, Wolfgang A. Herrmann, Verlag Chemie, 1996, pp. 258-268).

The disadvantage of processes with homogeneous catalysis is that the catalyst leaves the reactor together with the reaction products and unreacted starting materials, and must be separated from them. This necessitates work-up steps and gives rise to waste streams. Possible degradation products of the catalyst cannot be regenerated in situ to form the active catalyst, and this entails additional catalyst costs.

These disadvantages do not apply to olefin oligomerization processes with heterogeneous catalysis. Oligomerization over acidic catalysts—in industry, for example, zeolites or phosphoric acid on supports are employed—is well established. This produces isomer mixtures of branched oligomers. Even under optimized conditions, in the case of the oligomerization of linear butenes, the highly branched dimethylhexenes remain the principal product. One example of the acidic catalysis of oligomerizations of olefins is found in WO 92/13818.

For the non-acidic, heterogeneously catalysed oligomerization of olefins, it is common in industry to use nickel compounds on support materials. One catalyst of this kind is a nickel fixed bed catalyst which is employed in the Applicant's OCTOL process (Hydrocarbon Process., Int. Ed. 1986, Vol. 65, pp. 31-33).

Further nickel fixed bed catalysts with these properties are described in DE 43 39 713, in WO 95/14647 and in WO 99/25668, for example.

The non-acidic, heterogeneously catalysed oligomerization of olefins leads, under optimized conditions, to products having a higher linearity than with the acidic heterogeneous catalysts. Nevertheless, there are limits to the linearity of the products. Thus, for example, in the Octol process of the applicant, the iso index is greater than 1, and the level of production of the unwanted dimethylhexenes is around 15% to 30%. Homogeneous molecular catalysts, as a result of possibilities for varying the ligands, and as a result of their more highly defined structure, possess a greater potential for optimizations, and hence lead frequently to oligomerization catalysts whose selectivity for linear products is higher, and with which dimethylhexenes are produced as reaction products to a lesser degree.

A disadvantage which occurs both with homogeneous and with heterogeneous catalysts is the sharply falling selectivity for dimeric reaction products at high conversions. With increasing conversions there is a sharp increase in particular in the fraction of trimeric, tetrameric and higher oligomers. This results in increased cost and complexity for product separation, and in losses in yields, or else, if the higher oligomers can be used alternatively, which is economic only in the case of large oligomerization plants, leads to a higher cost and complexity for logistics and storage. With relatively small reactant streams in particular, therefore, it is advantageous if trimers, tetramers and higher oligomers are produced in the reaction not at all or only to a small extent.

A particularly high selectivity for dimeric oligomerization products is frequently achieved through the use of a 2-phase reaction regime. In this case the catalyst is located in a polar phase, while the products are located in—or themselves form—an apolar phase. Accordingly, in the catalyst phase, the dimers that are desired as reaction products are available only to a small extent for consecutive reactions to higher oligomers. One example of the application of a 2-phase reaction regime with an ionic liquid as polar catalyst phase is the DIFASOL process (Gilbert et al., Oil & Gas Science and Technology—Rev. IFP 2007, Vol. 62, pp. 745-759).

Disadvantages of the 2-phase reaction regime, however, are the limited concentration of the reactant olefins in the catalyst phase (particularly in the case of reactants having more than 4 carbon atoms), the slow mass transfer, the need for phase separation between reaction component and work-up component of the process, and the need—frequently—for large quantities of solvents.

The object, therefore, was to combine the advantages of a heterogeneously catalysed reaction, such as uncomplicated processing of the reaction mixture and ease of product separation, for example, with the advantages of a homogeneously catalysed reaction, such as high conversions and a simpler capacity for optimization leading to higher selectivities, for example.

It has now been found that Supported Ionic Liquid Phase catalysts—SILP catalysts for short—can be utilized in the oligomerization of $C_3$ to $C_5$ olefins. SILP catalysts are catalysts in piece form which are composed of a solid support material enveloped with an ionic liquid in which the active catalytic composition is present in solution. The principle of the immobilization of a molecular catalyst in a film of an ionic liquid on a solid support was first described in WO 2002098560.

The present invention provides a catalyst system composed of:
a) a support material selected from at least one of the following materials: silicon dioxide, aluminium oxide, magnesium oxide, zirconium oxide and mixed oxides thereof, carbon nanotubes;
b) an ionic liquid;
c) a catalytically active composition comprising nickel;
d) an activator selected from the group of Lewis acids with alkylating properties.

The present invention further provides a process for oligomerizing olefins having 3 to 5 carbon atoms using the catalysts of the invention.

The invention provides more particularly a process for preparing a mixture of $C_8$ olefins from a mixture of 1-butene, cis- and trans-2-butene and the unreactive component n-butane.

The present invention has the following advantages over conventional processes:
a) As catalysts in piece form, SILP catalysts have the typical advantages of heterogeneous catalysts as described in Jens Hagen, *Industrial Catalysis: A Practical Approach*, 2006, 2nd Ed., Wiley-VCH, p. 12.
b) In contrast to 2-phase systems, there is no need for phase separation between reaction component and work-up component and also solvents.
c) Since the actual catalyst is a molecular complex, the SILP catalysts have the typical advantages of homogeneous catalysts as described in Jens Hagen, *Industrial Catalysis: A Practical Approach*, 2006, 2nd Ed., Wiley-VCH, p. 12.
d) A further particular advantage with the process of the invention is the high linearity of the products and particularly the low level of formation of dimethylhexenes.
e) Since the catalytically active component is present in a polar phase, the selectivity for dimeric reaction products is very high. The polar phase is only a thin film, however, and so mass transport usually has no limiting effect.

The process of the invention is described in more detail below.

a) Support Material

Suitable support materials for the catalysts of the invention include carbon nanotubes, activated carbon, magnesium oxide, aluminium oxide, zirconium oxide and silicon dioxide and also their mixed oxides. For adjusting the acidity, the support materials may contain up to 1.5% by mass of alkali metal oxides. Furthermore, hydroxyl groups on the surface of the support materials may be dehydroxylated and/or protected with organosilicon radicals.

It is preferred to use silicon dioxide and activated carbon as support materials. Particular preference is given to using silicon dioxide having a particle size of between 0.05 mm and 4 mm and a BET surface area of 250 to 1000 m²/g, as determined in accordance with DIN 66131 and 66132, and also activated carbon having a BET surface area of between 1000 and 4000 m²/g. It is especially preferred to use silica gel having a particle size of between 0.063 mm and 0.2 mm and a BET surface area of between 300 and 800 m²/g.

b) Ionic Liquid

As ionic liquid for the catalysts of the invention, compounds are used in which the anion is selected from the group consisting of tetrafluoroborate ($[BF_4]^-$), hexafluorophosphate ($[PF_6]^-$), dicyanamide ($[N(CN)_2]^-$), bistrifluoromethylsulphonylamide ($[NTf_2]^-$), tricyanomethide ($[C(CN)_3]^-$), tetracyanoborate ($[B(CN)_4]^-$), halides ($Cl^-$, $Br^-$, $F^-$, $I^-$), hexafluoroantimony ($[SbF_6]^-$), hexafluoroarsenate ($[AsF_6]^-$), sulphate ($[SO_4]^{2-}$), tosylate ($[C_7H_7SO_3]^-$), nonaflate ($[C_4F_8SO_3]^-$), tris-(pentafluoroethyl)trifluorophosphate ($[PF_3(C_2F_5)_3]^-$), thiocyanate ($[SCN]^-$), carbonate ($[CO_3]^{2-}$), $[R'—COO]^-$, $[R'—SO_3]^-$, $[R'PO_4R'']^-$ or $[(R'—SO_2)2N]^-$, and R' and R" are identical or non-identical, each being a linear or branched, 1 to 12 carbon-atom-containing, aliphatic or alicyclic alkyl radical or a $C_5$-$C_{18}$ substituted aryl, $C_5$-$C_{18}$ substituted aryl-$C_1$-$C_6$-alkyl or $C_1$-$C_6$-alkyl-$C_5$-$C_{18}$ substituted aryl radical, which may be substituted by halogen atoms. The anion may also be introduced by mixing halides ($Cl^-$, $Br^-$, $F^-$, $I^-$) with Lewis-acidic compounds, such as aluminium compounds of the general empirical formula $Al_2X_nR_{6-n}$ with n=0-6, with $X=Cl^-$ or $Br^-$ and $R=C_1$-$C_6$ alkyl or $C_5$-$C_{12}$ cycloalkyl, or mixtures of these compounds, it being necessary for the molar fraction of aluminium halides to be greater than or equal to the fraction of the halides.

The cation is selected from:

quaternary ammonium cations of the general formula $[NR^1R^2R^3R^4]^+$, phosphonium cations of the general formula $[PR^1R^2R^3R^4]^+$, imidazolium cations of the general formula

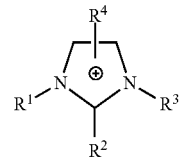

where the imidazole nucleus may be substituted by at least one group selected from $C_1$-$C_6$ alkyl, $C_1$-$C_6$ alkoxy, $C_1$-$C_6$ substituted aminoalkyl, $C_5$-$C_{12}$ substituted aryl or $C_5$-$C_{12}$ substituted aryl-$C_1$-$C_6$ alkyl groups, pyridinium cations of the general formula

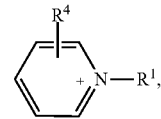

where the pyridine nucleus may be substituted by at least one group selected from $C_1$-$C_6$ alkyl, $C_1$-$C_6$ alkoxy, $C_1$-$C_6$ substituted aminoalkyl, $C_5$-$C_{12}$ substituted aryl or $C_5$-$C_{12}$ substituted aryl-$C_1$-$C_6$ alkyl groups, pyrazolium cations of the general formula

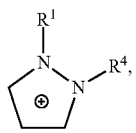

where the pyrazole nucleus may be substituted by at least one group selected from $C_1$-$C_6$ alkyl, $C_1$-$C_6$ alkoxy, $C_1$-$C_6$ substituted aminoalkyl, $C_5$-$C_{12}$ substituted aryl or $C_5$-$C_{12}$ substituted aryl-$C_1$-$C_6$ alkyl groups; and triazolium cations of the general formula

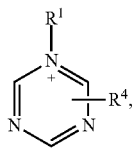

where the triazole nucleus may be substituted by at least one group selected from $C_1$-$C_6$ alkyl, $C_1$-$C_6$ alkoxy, $C_1$-$C_6$ substituted aminoalkyl, $C_5$-$C_{12}$ substituted aryl or $C_5$-$C_{12}$ substituted aryl-$C_1$-$C_6$ alkyl groups,
and the radicals $R^1$, $R^2$, $R^3$ are selected independently of one another from the group consisting of the following:
  hydrogen;
  linear or branched, saturated or unsaturated, aliphatic or alicyclic alkyl groups having 1 to 20 carbon atoms;
  heteroaryl, heteroaryl-$C_1$-$C_6$ alkyl groups having 3 to 8 carbon atoms in the heteroaryl radical and at least one heteroatom selected from N, O and S, which may be substituted by at least one group selected from $C_1$-$C_6$ alkyl groups and/or halogen atoms;
  aryl, aryl-$C_1$-$C_6$ alkyl groups having 5 to 12 carbon atoms in the aryl radical, which optionally may be substituted by one or more $C_1$-$C_6$ alkyl groups and/or halogen atoms;
and the radical $R^4$ is selected from:
  linear or branched, saturated or unsaturated, aliphatic or alicyclic alkyl groups having 1 to 20 carbon atoms;
  heteroaryl-$C_1$-$C_6$ alkyl groups having 4 to 8 carbon atoms in the aryl radical and at least one heteroatom selected from N, O and S, which may be substituted by one or more $C_1$-$C_6$ alkyl groups and/or halogen atoms;
  aryl-$C_1$-$C_6$ alkyl groups having 5 to 12 carbon atoms in the aryl radical, which optionally may be substituted by one or more $C_1$-$C_6$ alkyl groups and/or halogen atoms.

In the process of the invention it is preferred to use ionic liquids with the following anions:
mixtures of halides (Cl$^-$, Br$^-$, F$^-$, I$^-$) with aluminium halides (AlX$_3$ with X=Cl, Br, F, I), it being necessary for the molar fraction of aluminium halides to be greater than or equal to the fraction of the halides, tetrafluoroborate ([BF$_4$]$^-$), hexafluorophosphate ([PF$_6$]$^-$), bistrifluoromethylsulphonylamide ([NTf$_2$]$^-$), hexafluoroantimonate ([SbF$_6$]$^-$), hexafluoroarsenate ([AsF$_6$]$^-$), tris(pentafluoroethyl)trifluorophosphate ([PF$_3$(C$_2$F$_5$)$_3$]$^-$).

It is particularly preferred to use mixtures of halides (Cl$^-$, Br$^-$, F$^-$, I$^-$) with Lewis-acidic compounds, such as aluminium compounds of the general empirical formula $Al_2X_nR_{6-n}$ with n=0-6, with X=Cl$^-$ or Br$^-$ and R=$C_1$-$C_6$ alkyl or $C_5$-$C_{12}$ cycloalkyl, or mixtures of these compounds, it being necessary for the molar fraction of aluminium halides to be greater than or equal to the fraction of the halides. It is especially preferred to use mixtures of chloride anions with aluminium trichloride having a molar fraction of the aluminium trichloride of 55%, or the anion tris(pentafluoroethyl)trifluorophosphate ([PF$_3$(C$_2$F$_5$)$_3$]$^-$) (FAP).

The process of the invention preferably uses ionic liquids having the following cations:

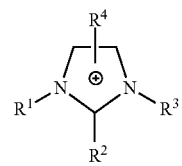

where the imidazole nucleus may be substituted by at least one group selected from $C_1$-$C_6$ alkyl, $C_1$-$C_6$ alkoxy, $C_1$-$C_6$ substituted aminoalkyl, $C_5$-$C_{12}$ substituted aryl or $C_5$-$C_{12}$ substituted aryl-$C_1$-$C_6$ alkyl groups.

Particular preference is given to using the $C_1$-$C_4$ alkyl-substituted imidazole cation.

c) Catalytically Active Composition

In solution in the ionic liquid of the catalyst in piece form is the catalytically active composition, composed of a nickel complex, its precursor(s) and optionally an activator. In the process of the invention, the catalytically active composition is generated from one or more precursors and optionally an activator, under process conditions, or is supplied to the process already in the form of an active catalyst.

d) Precursors

As precursors to the catalytically active nickel complex it is possible to use all nickel compounds which are soluble in the ionic liquid and have the formal oxidation state 0 or +2. Preference is given to using NiX$_2$ (with X=Cl, Br), Ni(acetylacetonato)$_2$, Ni(hexafluoroacetylacetonato)$_2$, Ni(cyclooctadienyl)$_2$, Ni(cyclopentadienyl)$_2$, Ni$_2$($\eta^3$-allyl)($\mu$-Cl$_2$), Ni$_2$($\eta^3$-allyl)($\mu$-Br$_2$), Ni$_2$($\eta^3$-methallyl)($\mu$-Cl$_2$), Ni$_2$($\eta^3$-methallyl)($\mu$-Br$_2$), Ni($\eta^3$-allyl)$_2$, Ni($\eta^3$-methallyl)$_2$, NiX$_2$(PR$^1$R$^2$R$^3$)$_2$ (with X=Cl, Br and R$^1$, R$^2$, R$^3$=$C_1$-$C_8$ alkyl, $C_5$-$C_{12}$ aryl, it not being necessary for R$^1$, R$^2$ and R$^3$ to be identical). Particular preference is given to using NiCl$_2$(PPh$_3$)$_2$.

As an additional precursor it is possible if desired to use phosphorus compounds having the formal oxidation state +3. Preference is given to using compounds of the general formula PR$^1$R$^2$R$^3$ with R$^1$, R$^2$, R$^3$=$C_1$-$C_8$ alkyl, $C_5$-$C_{12}$ substituted aryl radical, compounds of the general formula P(XR$^1$)(XR$^2$)(XR$^3$) with R$^1$, R$^2$, R$^3$=$C_1$-$C_8$ alkyl, $C_5$-$C_{12}$ substituted aryl radical, and X=N, O. Particular preference is given to using compounds of the general formula PR$^1$R$^2$R$^3$ with R$^1$, R$^2$, R$^3$=$C_5$-$C_{12}$ substituted aryl radical.

As an additional precursor it is possible if desired to use 1,3-diketones. Preference is given to using 1,1,1,5,5,5-hexafluoroacetylacetone, 2,2,2-trifluoro-N-(2,2,2-trifluoroacetyl)acetamide and acetylacetone.

d) Activator

As activator it is possible in the process of the invention to use Lewis acids with alkylating properties. Preference is given to using compounds having the general empirical formula $Al_2X_nR_{6-n}$ with n=1-5, R=$C_1$-$C_6$ alkyl or $C_5$-$C_{12}$ substituted cycloalkyl radical and X=Cl$^-$ or Br$^-$. Very particular preference is given to using ethylaluminium dichloride.

Relative Proportions of the Components

Generally speaking, the realizable mass ratio of ionic liquid to support material is dependent on physical properties. Particularly critical for the ionic liquid is the density, and for the support material the pore volume. More specifically, the pore radius distribution of the support, and the wetting characteristics of the ionic liquid on the surface of the support, have an influence.

Depending on the support material and on the nature of the ionic liquid, the ionic liquid may be applied in a wide mass ratio relative to the support. For silicon dioxide supports whose hydroxyl groups on the surface of the support materials have been dehydroxylated or protected with organic silicon radicals, it is possible to use mass ratios of the preferably used ionic liquid (1-butyl-3-methylimidazolium chloride/aluminium chloride) to the support of 0.007 to 0.674. Preference is given to mass ratios of 0.034 to 0.334. Particularly preferred is the range from 0.067 to 0.169. For activated carbon supports it is preferred to use ratios of 0.022 to 2.171. Particularly preferred are mass ratios of 0.217 to 0.543. For the particularly preferred silicon dioxide supports, mass ratios of ionic liquid to support material of 0.012 to 1.255 are used with preference. Particularly preferred are ratios of 0.063 to 0.628. Especially preferred are ratios of 0.126 to 0.314.

The realizable mass ratios of nickel to ionic liquid are generally dependent on the nature of ionic liquid and on the nature of the support material.

For the particularly preferred silicon dioxide supports, the particularly preferred mass ratios of ionic liquid to support material are from 0.126 to 0.314. Mass ratios of nickel to ionic liquid of 0.003 to 0.027 are used. Preferred are ratios of 0.010 to 0.020. Particularly preferred is the ratio from 0.010 to 0.011.

Catalyst Preparation

The catalysts of the invention can be prepared by treating the solid support material with a homogeneous solution comprising the other catalyst components and optionally a solvent.

One way is to impregnate the solid support material with a solution of this kind. In that case an excess of solution is added to the support material. Following mass transfer between support material and solution, which may be accelerated by shaking or stirring, the excess liquid is removed mechanically from the catalyst in piece form, by filtration or centrifuging, for example. This may be followed by a drying step.

Another method is to spray the support material with a solution of this kind. If desired, any added solvent is removed during or after the spraying operation.

The catalyst is prepared preferably by adding to the support material a solution which is composed of the other catalyst components and a solvent, and evaporating the solvent. Solvents used for this purpose are preferably low-boiling compounds which form a homogeneous solution with the other catalyst components and which do not react with any of these components. Examples of suitable solvents include dichloromethane, hexane and toluene. One especially preferred solvent is dichloromethane.

The solvent is separated off in the pressure range from $10^5$ to $2*10^2$ Pa, with the pressure being lowered successively, starting from atmospheric pressure. In order to prevent decomposition of the catalyst during the catalyst preparation procedure, the preparation procedure takes place in the absence of oxygen and of water.

The supported catalysts of the invention are prepared preferably in a form which offers a low flow resistance during the oligomerization. Typical forms are tablets, cylinders, strand extrudates or rings. The shaping in this case takes place generally on the support material prior to application of the ionic liquid and of the catalyst components in solution therein. It is also possible to use granular supports for preparing the catalysts of the invention. By extractive sieving it is possible in that case to separate out a catalyst support having the desired particle size. Support materials can frequently be obtained commercially as shaped bodies.

Feedstocks

Over the catalysts of the invention it is possible to oligomerize olefins having 3 to 5 carbon atoms to form olefins having 6 to 10 carbon atoms. It is possible in principle to use all olefins or olefin mixtures having 3 to 5 carbon atoms, irrespective of the position of the double bond. The feed stocks may be composed of olefins with the same, similar (±2) or markedly different (>2) C number.

It is noted that not only the aforementioned olefins but also mixtures thereof with saturated hydrocarbons may be used.

In the process of the invention it is preferred to use 2-butenes and 1-butene. Used more particularly are mixtures of 2-butenes, 1-butene, and linear and branched butanes, of the kind produced in the work-up of the $C_4$ cut from a steam-cracker after the removal of the polyunsaturated compounds and of the isobutene. These techniques are described in the art literature (K. Weissermel, H. J. Arpe, Industrielle Organische Chemie, Wiley-VCH, 5th edition, 1998).

Process Implementation

EXAMPLES

The examples which follow are intended to illustrate the invention.

Example 1

Inventive: Preparation of an SILP Catalyst with the Ionic Liquid (IL) 1-butyl-3-methylimidazolium chloride ([BMIM]Cl)/Aluminium Chloride and the Catalyst Precursor $NiCl_2(PPh_3)_2$ All operating steps are carried out in an inert gas box or using the Schlenk technique. To prepare a catalyst charge for a batch experiment, 147.1 mg of $NiCl_2(PPh_3)_2$ (available commercially) and 471.6 mg of triphenylphosphine (available commercially) are weighed out into a 100 ml Schlenk flask. 20 ml of dry dichloromethane (water content <20 ppm) are added and the mixture is stirred for 15 minutes on a magnetic stirrer. Then 4.0 g of silica gel (particle size 0.063-0.200 mm, BET surface area 315 $m^2$/g, pore volume 0.996 ml/g) are added and the suspension is stirred for 15 minutes more. Then 1.26 g of [BMIM]Cl/$AlCl_3$ (molar fraction of $AlCl_3$: 55%) are weighed out. After a further 15 minutes on the magnetic stirrer, the flask, in a water bath at room temperature, is attached to a vacuum pump and the pressure is reduced slowly from $10^5$ Pa to $2*10^2$ Pa. After about 45 minutes, a turquoise powder is present.

Description of the Oligomerization Apparatus

A flow diagram of the stirred tank reactor used for the batch dimerization is shown in FIG. 1. The Hastelloy autoclave possesses a motor-driven stirring unit (gas introduction stirrer, Heidolph RZR 2020 motor) and also a pressure indicator (PI) and temperature indicator (TI 1). The overpressure valve V-5, which opens at 80 bar, prevents an excessive, unwanted increase in pressure within the reactor. Via the valves V-1, V-2 and V-3 it is possible to pass reactants and also inert gas into the stirred tank. Samples can be taken during a catalyst experiment via valve V-4.

Description of the Experimental Procedure

To carry out a batch dimerization experiment, the procedure adopted was as follows: using the Schlenk technique, the SILP powder prepared was inserted into the reactor under inert gas conditions, and the reactor was screwed shut. Through an opening in the lid, 80 ml of cyclohexane (water content <20 ppm) were introduced. Approximately 1 ml of n-nonane as internal GC standard and 6 ml of ethylaluminium dichloride (0.1 molar solution in hexane, available commercially) were added, and the opening in the lid was closed.

At V-3, a steel cylinder with 22 g of reactant was attached, and this reactant was introduced into the reactor a short time before the beginning of the experiment. When the stirrer was started at 1000 l/min, recording of the time was commenced. Samples were taken from the reactor via valve V-4. The samples were hydrogenated prior to analysis by gas chromatography. This made it easy to separate the differently branched products from one another.

Inventive Experimental Results

The preparation of the catalytically active composition and the implementation of the experiments were in accordance with the procedures described above. The reactant employed was a mixture of 70% n-butane, 19% trans-2-butene, 9% cis-2-butene, 1.7% 1-butene and 0.3% isobutane+$C_5$ alkanes. The reactant mass is based on the mixture. The conversion is based only on the butenes present.

Entry 4 from Table 1 shows the use of silica gel which has been dehydroxylated by silylation. Here, again, a very good iso index of <1 is achieved. The particular feature of this example is that very little ionic liquid is needed, as illustrated by what is by far the lowest IL/support material ratio, with a value of 0.067.

Comparison with the Prior Art:
Comparison with Conventional Homogeneous Catalysis:

The purely homogeneously catalysed Dimersol process referred to at the outset (see Yves Chauvin, Helene Olivier, in "Applied Homogeneous Catalysis with Organometallic Compounds", edited by Boy Cornils, Wolfgang A. Herrmann, Verlag Chemie, 1996, pp. 258-268) produces up to 40% of dimethylhexenes. The iso index is typically 1 to 1.35, and the selectivity for $C_8$ oligomers in that process is <90%. In other words, the catalyst systems of the invention are superior to the Dimersol process in respect both of selectivity for $C_8$ oligomers and of linearity of the products, and particularly with respect to a low dimethylhexene selectivity. Furthermore, the reaction regime with the catalyst systems of the invention is considerably simpler, since on account of their immobilized character they can be separated easily from the products.

Comparison with Conventional Heterogeneous Catalysis:

In the case of the purely heterogeneously catalysed process, the selectivity for dimethylhexenes is around 15% to 30%, with an iso index which is typically >1. The dimer selectivity is <90% (see Albers et al., Oligomerisation of

TABLE 1

Example experimental results with the inventive catalyst system: catalyst precursor $NiCl_2(PPh_3)_2$; temperature: 20° C.; activator: 6 ml $EtAlCl_2$ solution (0.1 molar solution in hexane)

| No. | Ionic liquid | Support material | IL/support material [—] | Conversion 60 min [%] | $S_{C8}$ [%] | Iso index [—] | $S_{DMH}$ [%] | $S_{MH}$ [%] | $S_{Oct}$ [%] |
|---|---|---|---|---|---|---|---|---|---|
| 1 | [BMIM]Cl/AlCl$_3$ | Silica | 0.126 | 69.4 | 94.2 | 1.0 | 11.6 | 76.8 | 11.6 |
| 2 | [EMIM][FAP] | Silica | 0.171 | 12.6 | 98.8 | 0.97 | 9.9 | 77.1 | 13.0 |
| 3 | [BMIM]Cl/AlCl$_3$ | Activated carbon | 0.217 | 40.3 | 94.2 | 0.96 | 7.6 | 81.0 | 11.4 |
| 4 | [BMIM]Cl/AlCl$_3$ | Si silica | 0.067 | 33.7 | 97.8 | 0.97 | 9.8 | 77.2 | 13.0 |

[BMIM]Cl/AlCl$_3$ = 1-butyl-3-methylimidazolium chloride/aluminium chloride (ratio 1/1.1),
[EMIM][FAP] = 1-ethyl-3-methylimidazolium tris(pentafluoroethyl)tri-fluorophosphate, silica gel: Merck KGaA type 10184 (particle size 0.063-0.200 mm, BET surface area 315 m$^2$/g, pore volume 0.996 ml/g), activated carbon: Fluka activated carbon (powder, BET surface area 2056 m$^2$/g, pore volume 1.723 ml/g), Si silica: Silica 60, silanized: Merck KGaA (particle size 0.063-0.200 mm, BET surface area 430 m$^2$/g, pore volume 0.535 ml/g).

Entry 1 from Table 1 shows that, with the inventive catalyst system using $NiCl_2(PPh_3)_2$, ethylaluminium dichloride as activator, a mixture of 1-butyl-3-methylimidazolium chloride and aluminium chloride in a ratio of 1/1.1 as ionic liquid, and silica gel as support material, it is possible to obtain a C4 hydrocarbon having a low olefin content of approximately 30%, a very high selectivity of 94% for the desired dimeric reaction products and at the same time a low selectivity (11.6%) for the unwanted dimethylhexene. The iso index is 1.

Entry 2 from Table 1 shows the use of 1-ethyl-3-methylimidazolium tris(pentafluoroethyl)trifluorophosphate as an ionic liquid under otherwise identical conditions. Here, even higher selectivities for the $C_8$ oligomers are obtained, but the conversion is lower. The selectivity for dimethylhexenes is very low, at about 10%. At the same time a very good iso index of <1 is obtained.

Entry 3 from Table 1 shows the use of activated carbon as support material. Here, at 7%, the selectivity for dimethylhexenes is particularly low, and a particularly low iso index, for a conversion of 40%, is achieved.

$C_3$-$C_5$ on Solid State Nickel Compounds: Complex Catalysts for a versatile Reaction, DGMK-Tagungsbericht 2004-3). In other words, the catalyst systems of the invention are superior to this process in respect both of the selectivity for $C_8$ oligomers and of the linearity of the products, particularly with respect to a low dimethylhexene selectivity.

Liquid-Liquid 2-Phase Reaction Mode:

Using NiCl2(PPh3)2, ethylaluminium dichloride as activator and 1-butyl-3-methylimidazolium chloride/aluminium chloride (ratio 1/1.1) as polar phase in a liquid-liquid 2-phase reaction mode, selectivities of 20% to 30% for dimethylhexenes and an iso index of >1 are observed (see Gilbert et al., Oil & Gas Science and Technology—Rev. IFP 2007, Vol. 62, pp. 745-759). The selectivity for dimers, at around 95%, is at a similar level as with the catalyst systems of the invention. With respect to the linearity of the products and the dimethyl selectivity, however, the catalyst systems of the invention are superior.

The invention claimed is:

1. A process for oligomerizing an unsaturated hydrocarbon mixture, the process comprising oligomerizing an unsaturated hydrocarbon mixture in the presence of a catalyst, comprising:
   a) at least one support material selected from the group consisting of silicon dioxide, aluminium oxide, magnesium oxide, zirconium oxide, mixed oxides thereof, activated carbon, and carbon nanotubes, wherein hydroxyl groups on a surface of the support material are dehydroxylated, protected with organosilicon radicals, or both;
   b) an ionic liquid;
   c) a catalytically active composition comprising nickel; and
   d) an activator comprising a Lewis acid with alkylating properties,
   wherein the iso index obtained by oligomerizing the unsaturated hydrocarbon mixture is less than 1.

2. The process of claim 1, wherein the ionic liquid comprises:
   at least one anion selected from the group consisting of tetrafluoroborate, hexafluorophosphate, dicyanamide, bistrifluoromethylsulphonylamide, tricyanomethide, tetracyanoborate, a halide, hexafluoroantimonate, hexafluoroarsenate, sulphate, tosylate, nonaflate, tris(pentafluoroethyl)trifluorophosphate, thiocyanate, carbonate, [R″—COO]$^-$, [R′—SO$_3$]$^-$, [R′PO$_4$R″]$^-$ and [(R′—SO$_2$)$_2$N]$^-$, wherein R′ and R″ independently represent an identical or non-identical, linear or branched, 1- to 12 carbon-atom-containing, aliphatic or alicyclic alkyl radical or a C$_5$-C$_{18}$ substituted aryl, C$_5$-C$_{18}$ substituted aryl-C$_1$-C$_6$-alkyl or C$_1$-C$_6$-alkyl-C$_5$-C$_{18}$ substituted aryl radical, optionally substituted with at least one halogen atom; and
   at least one cation selected from the group consisting of:
      a quaternary ammonium cation of formula [NR$^1$R$^2$R$^3$R$^4$]$^+$;
      a phosphonium cation of formula [PR$^1$R$^2$R$^3$R$^4$]$^+$;
      an imidazolium cation of formula (I):

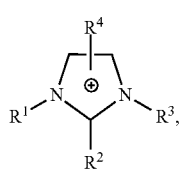

(I)

wherein the imidazole nucleus is optionally substituted with at least one group selected from the group consisting of a C$_1$-C$_6$ alkyl, a C$_1$-C$_6$ alkoxy, a C$_1$-C$_6$ substituted aminoalkyl, a C$_5$-C$_{12}$ substituted aryl, and a C$_5$-C$_{12}$ substituted aryl-C$_1$-C$_6$ alkyl;
      a pyridinium cation of formula (II):

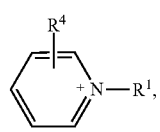

(II)

wherein the pyridine nucleus is optionally substituted with at least one group selected from the group consisting of a C$_1$-C$_6$ alkyl, a C$_1$-C$_6$ alkoxy, a C$_1$-C$_6$ substituted aminoalkyl, a C$_5$-C$_{12}$ substituted aryl, and a C$_5$-C$_{12}$ substituted aryl-C$_1$-C$_6$ alkyl;
      a pyrazolium cation of formula (III):

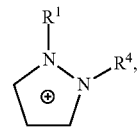

(III)

wherein the pyrazole nucleus is optionally substituted with at least one group selected from the group consisting of a C$_1$-C$_6$ alkyl, a C$_1$-C$_6$ alkoxy, a C$_1$-C$_6$ substituted aminoalkyl, a C$_5$-C$_{12}$ substituted aryl, and a C$_5$-C$_{12}$ substituted aryl-C$_1$-C$_6$ alkyl; and
      a triazolium cation of formula (IV):

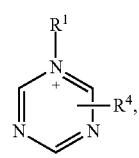

(IV)

wherein the triazole nucleus is optionally substituted with at least one group selected from the group consisting of a C$_1$-C$_6$ alkyl, a C$_1$-C$_6$ alkoxy, a C$_1$-C$_6$ substituted aminoalkyl, a C$_5$-C$_{12}$ substituted aryl, and a C$_5$-C$_{12}$ substituted aryl-C$_1$-C$_6$ alkyl
   wherein:
   the radicals R$^1$, R$^2$, R$^3$ are independently selected from the group consisting of:
      hydrogen;
      a linear or branched, saturated or unsaturated, aliphatic or alicyclic alkyl group having 1 to 20 carbon atoms;
      a heteroaryl group,
      a heteroaryl-C$_1$-C$_6$ alkyl group having 3 to 8 carbon atoms in the heteroaryl radical and at least one heteroatom selected from the group consisting of N, O and S, optionally substituted with at least one group selected from the group consisting of a C$_1$-C$_6$ alkyl group, and a halogen atom;
      an aryl group; and
      an aryl-C$_1$-C$_6$ alkyl group having 5 to 12 carbon atoms in the aryl radical, optionally substituted by at least one C$_1$-C$_6$ alkyl group, halogen atom, or both;
   the radical R$^4$ is selected from the group consisting of:
      a linear or branched, saturated or unsaturated, aliphatic or alicyclic alkyl group having 1 to 20 carbon atoms;
      a heteroaryl-C$_1$-C$_6$ alkyl group having 4 to 8 carbon atoms in the aryl radical and at least one heteroatom selected from the group consisting of N, O and S, optionally substituted with at least one C$_1$-C$_6$ alkyl group, halogen atom, or both; and
      an aryl-C$_1$-C$_6$ alkyl group having 5 to 12 carbon atoms in the aryl radical, optionally substituted with at least one C$_1$-C$_6$ alkyl group, halogen atom, or both.

3. The process of claim 1, wherein the catalytically active composition comprises nickel in a form soluble with the ionic liquid, and in a 0 to +2 oxidation state.

4. The process of claim 3, wherein the catalytically active composition comprises $NiCl_2(P(Ph)_3)_2$.

5. The process of claim 1, wherein the activator comprises an organic aluminium compound of formula $Al_2X_nR_{6-n}$, wherein:

n=0-6;

X=$Cl^-$ or $Br^-$; and

R=$C_1$-$C_6$ alkyl, $C_5$-$C_{12}$ cycloalkyl, or a mixture thereof.

6. The process of claim 1, wherein the activator comprises ethylaluminium dichloride.

7. The process of claim 1, wherein the ionic liquid comprises 1-butyl-3-methylimidazolium chloride and aluminium chloride.

8. The process of claim 1, wherein the ionic liquid comprises 1-ethyl-3-methylimidazolium tris(pentafluoroethyl) trifluorophosphate.

9. The process of claim 1, wherein the at least one support material comprises silicon dioxide having a particle size of 0.063 to 0.2 mm, and a BET surface area of 250 to 1000 $m^2/g$, determined in accordance with DIN 66131 and 66132.

10. The process of claim 1, wherein the at least one support material comprises silicon dioxide, and a mass ratio of the ionic liquid to the support material is from 0.012 to 1.255.

11. The process of claim 2, wherein the at least one support material comprises silicon dioxide which has been dehydroxylated, and a mass ratio of the ionic liquid to the support material is from 0.007 to 0.674.

12. The process of claim 2, wherein the at least one support material comprises activated carbon having a BET surface area of between 1000 $m^2/g$ and 4000 $m^2/g$ as determined in accordance with DIN 66131 and 66132, and a mass ratio of the ionic liquid to the support material is from 0.022 to 2.171.

13. The process of claim 1, wherein the unsaturated hydrocarbon mixture comprises a stream comprising an olefin having three to five carbon atoms.

14. The process of claim 1, wherein the unsaturated hydrocarbon mixture comprises a stream comprising a linear C4 olefin and a saturated hydrocarbon.

15. The process of claim 1, wherein the unsaturated hydrocarbon mixture comprises a stream comprising a mass fraction of between 50% and 80% of a saturated hydrocarbon and a linear C4 olefin.

16. The process of claim 2, wherein the at least one support material comprises silicon dioxide, and a mass ratio of the ionic liquid to the silicon dioxide is from 0.012 to 1.255.

17. The process of claim 1, wherein the hydroxyl groups on a surface of the support material are protected with organosilicon radicals.

* * * * *